US00PP33635P2

(12) United States Plant Patent
Mazzardis

(10) Patent No.: US PP33,635 P2
(45) Date of Patent: Nov. 16, 2021

(54) BLUEBERRY PLANT NAMED 'NS 16-7'

(50) Latin Name: ***Vaccinium* hybrid**
Varietal Denomination: NS 16-7

(71) Applicant: Next Progeny Pty., Ltd., Subiaco (AU)

(72) Inventor: Vincent David Andrew Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 17/336,801

(22) Filed: Jun. 2, 2021

(30) Foreign Application Priority Data

Aug. 28, 2020 (QZ) ..... PBR 2020/2016

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
See application file for complete search history.

(56) References Cited

U.S. PATENT DOCUMENTS

PP25,858 P3 9/2015 Mazzardis
PP25,859 P3 9/2015 Mazzardis
PP25,860 P3 9/2015 Mazzardis
PP25,889 P3 9/2015 Mazzardis
PP26,172 P3 12/2015 Mazzardis
PP26,173 P3 12/2015 Mazzardis
PP27,142 P3 9/2016 Mazzardis
PP28,149 P3 7/2017 Mazzardis
PP28,217 P3 7/2017 Mazzardis
PP28,334 P3 8/2017 Mazzardis
PP28,357 P3 9/2017 Mazzardis
PP28,358 P3 9/2017 Mazzardis
PP30,626 P3 7/2019 Mazzardis
PP30,755 P3 7/2019 Mazzardis
PP30,756 P3 7/2019 Mazzardis
PP30,846 P2 8/2019 Mazzardis
PP30,934 P3 10/2019 Mazzardis
PP32,745 P3 1/2021 Mazzardis
PP32,781 P3 2/2021 Mazzardis
PP32,823 P3 2/2021 Mazzardis
PP32,897 P3 3/2021 Mazzardis
PP33,087 P3 5/2021 Mazzardis
PP33,154 P3 5/2021 Mazzardis
PP33,112 P3 6/2021 Mazzardis
PP33,137 P3 6/2021 Mazzardis
PP33,138 P3 6/2021 Mazzardis
2021/0051827 P1 2/2021 Mazzardis

*Primary Examiner* — Susan McCormick Ewoldt
(74) *Attorney, Agent, or Firm* — Randall Danskin, P.S.

(57) ABSTRACT

A new and distinct variety of blueberry plant, which is denominated varietally as 'NS 16-7' is described, with a strong plant vigor and which produces fruit considered large in size, high to very high in sweetness, and firm under the ecological conditions prevailing in Yanchep, Western Australia.

2 Drawing Sheets

Latin name: *Vaccinium* hybrid.

Variety denomination: The invention relates to a new, novel, and distinct variety of blueberry plant, a *Vaccinium* hybrid, with a variety denomination hereinafter as 'NS 16-7'.

CROSS REFERENCE TO RELATED APPLICATIONS

This application claims the benefit of priority under 35 USC § 119 to Community Plant Variety Office (CPVO) Application No. 2020/2016 for Community Plant Variety Rights, filed on Aug. 28, 2020 for a blueberry plant with a variety denomination of 'NS 16 7', which is herein incorporated by reference in its entirety.

SUMMARY

The new variety of blueberry plant resulted from an ongoing development program of plant breeding conducted to identify such plants. The purpose of the program was to improve the commercial quality of blueberry plants and other plant species. To this end, controlled, hybrid, crosspollinations were made in order to produce plant populations from which improved progeny were evaluated and thereafter selected.

The 'NS 16-7' blueberry plant was originated and selected from a population of new plants growing on the breeder's property, which is located at Yanchep Springs in Yanchep, Western Australia. The new variety of blueberry plant was derived from a controlled, hybrid, cross-pollination of the seed parent, blueberry plant 'EB 8-42' (U.S. Plant Pat. No. 25,858), and a pollen parent, blueberry plant 'EB 9-2' (U.S. Plant Pat. No. 28,149), during the 2013 growing season.

Prior Varieties

The seed parent 'EB 8-42' is characterized principally by a semi-upright growth habit, a medium to strong vigor, a very early season first pick date, and further produces large-sized, firm, medium to high sweetness, and low to medium acidity fruit under the ecological conditions occurring in Yanchep, Western Australia. Also, the seed parent 'EB 8-42' exhibits a very early date of bloom time, an August first pick date, and a December last pick date under the ecological conditions occurring in Yanchep, Western Australia. Further, the seed parent 'EB 8-42' is evergreen and produces fruit on one-year-old and current season's shoots.

The pollen parent 'EB 9-2', on the other hand, is characterized principally by an upright to semi-upright growth habit, a strong to very strong vigor, a very early season first pick date, and further produces large- to very-large-sized, firm to very firm, high sweetness, and low to medium acidity fruit under the ecological conditions occurring in Yanchep, Western Australia. Also, the pollen parent 'EB 9-2' exhibits a very early (February-March) date of bloom time, a March first pick date, and a December last pick date under the ecological conditions occurring in Yanchep, Western Australia. Further, the pollen parent 'EB 9-2' is evergreen and produces fruit on one-year-old and current season's shoots.

Origin

The seed from the seed parent 'EB 8-42' produced approximately 350 plants following cross-pollination. These new plants were then grown at the aforementioned property, and fruit from these new plants was first observed in 2015. A subsequent assessment of these same self-fertile, new plants conducted during the 2016 growing season and additionally during the 2017 growing season led to selecting the 'NS 16-7' variety for further evaluation.

Asexual Reproduction

The further evaluation included an asexual vegetative propagation, by vegetative cuttings, at Yanchep Springs in Yanchep, Western Australia. Subsequent evaluations of the newly derived plant in the 2018 growing season led to a conclusion that the 'NS 16-7' variety was a distinct and new variety of blueberry plant found to be true to the original plant. The new variety of blueberry plant was considered to be novel in view of its strong plant vigor, large fruit size, high to very high fruit sweetness, and firm level of fruit firmness.

Comparisons

In comparison to the seed parent 'EB 8-42' under the ecological conditions occurring in Yanchep, Western Australia, the new variety is noteworthy. In this regard, the seed parent has a plant vigor considered to be medium to strong. In contrast, the new variety of blueberry plant has a plant vigor considered to be strong. In addition, the seed parent and the new variety of blueberry plant both produce fruit with a size considered to be large. Also, the seed parent produces fruit considered to be medium to high in sweetness. This is in contrast to the fruit of the new variety of blueberry plant, which is considered to be high to very high in sweetness. Further, the seed parent and the new variety of blueberry plant both produce fruit considered to be firm.

In comparison to the pollen parent 'EB 9-2' under the ecological conditions occurring in Yanchep, Western Australia, the new variety is noteworthy. In this regard, the pollen parent has a plant vigor considered to be strong to very strong. In contrast, the new variety of blueberry plant has a plant vigor considered to be strong. In addition, the pollen parent produces fruit considered to be large to very large in size. This is in contrast to the fruit of the new variety of blueberry plant, which is considered to be large in size. Also, the pollen parent produces fruit considered to be high in sweetness. However, the fruit of the new variety of blueberry plant is considered to be high to very high in sweetness. Further, the pollen parent produces fruit considered to be firm to very firm. In contrast, the fruit of the new variety of blueberry plant is considered to be firm.

The new variety of blueberry plant is readily distinguishable from the most closely related, known variety, the pollen parent 'EB 9-2' blueberry plant described above.

The comparisons described above are summarized in Table 1 below.

TABLE 1

Summary of Comparisons

| | 'NS 16-7' | 'EB 8-42' (Seed) | 'EB 9-2' (Pollen) |
|---|---|---|---|
| Plant vigor | Strong | Medium to strong | Strong to very strong |
| Fruit size | Large | Large | Large to very large |
| Fruit sweetness | High to very high | Medium to high | High |
| Fruit firmness | Firm | Firm | Firm to very firm |

In addition, Table 2 below compares the 'NS 16-7' variety to a sibling cultivar that resulted from same the seed parent 'EB 8-42' and pollen parent 'EB 9-2', namely, 'NS 16-8' (U.S. Plant Pat. No. 33,137).

TABLE 2

Comparison to Sibling Cultivar

| | 'NS 16-7' | 'NS 16-8' |
|---|---|---|
| Plant vigor | Strong | Medium |
| Fruit size | Large | Large |
| Fruit sweetness | High to very high | Medium |
| Fruit firmness | Firm | Medium |

BRIEF DESCRIPTION OF THE DRAWINGS

The accompanying drawings are color photographs of the new blueberry plant 'NS 16-7' during the second year of growth under the ecological conditions prevailing at the breeder's property, which is located at Yanchep Springs in Yanchep, Western Australia.

Figure 1:
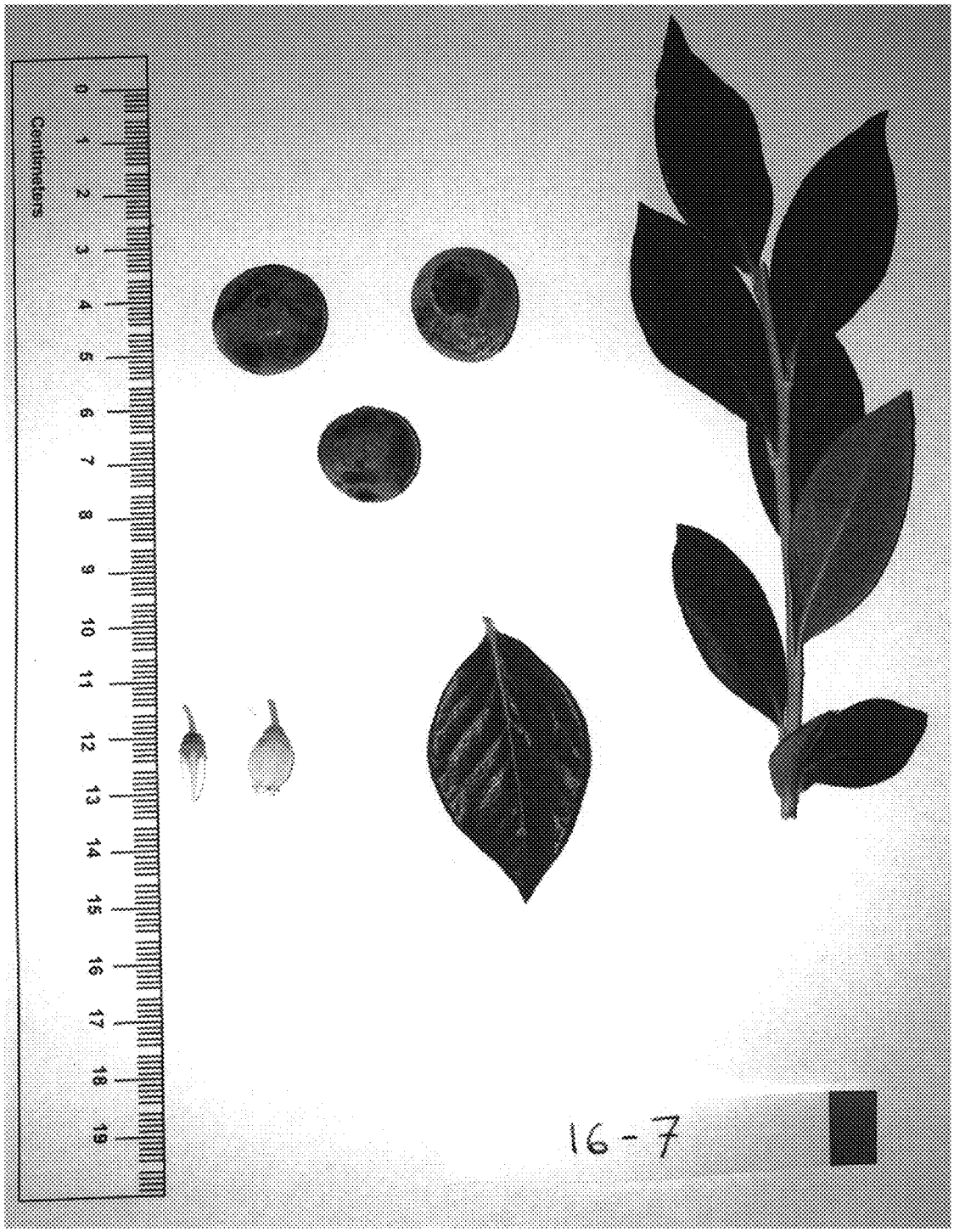
FIG. 1 is a color photograph, which shows fruit, blooms, leaves, and a portion of a vegetative stem of the new blueberry plant 'NS 16-7', the fruit being sufficiently mature for harvesting and shipment. This photograph also depicts the fruit size and the color of the ripe fruit, leaves showing the sizes and the upper and under side colorations thereof, two blooms at different stages of maturation, and additional leaves on the stem at different stages of maturation.
Figure 2:
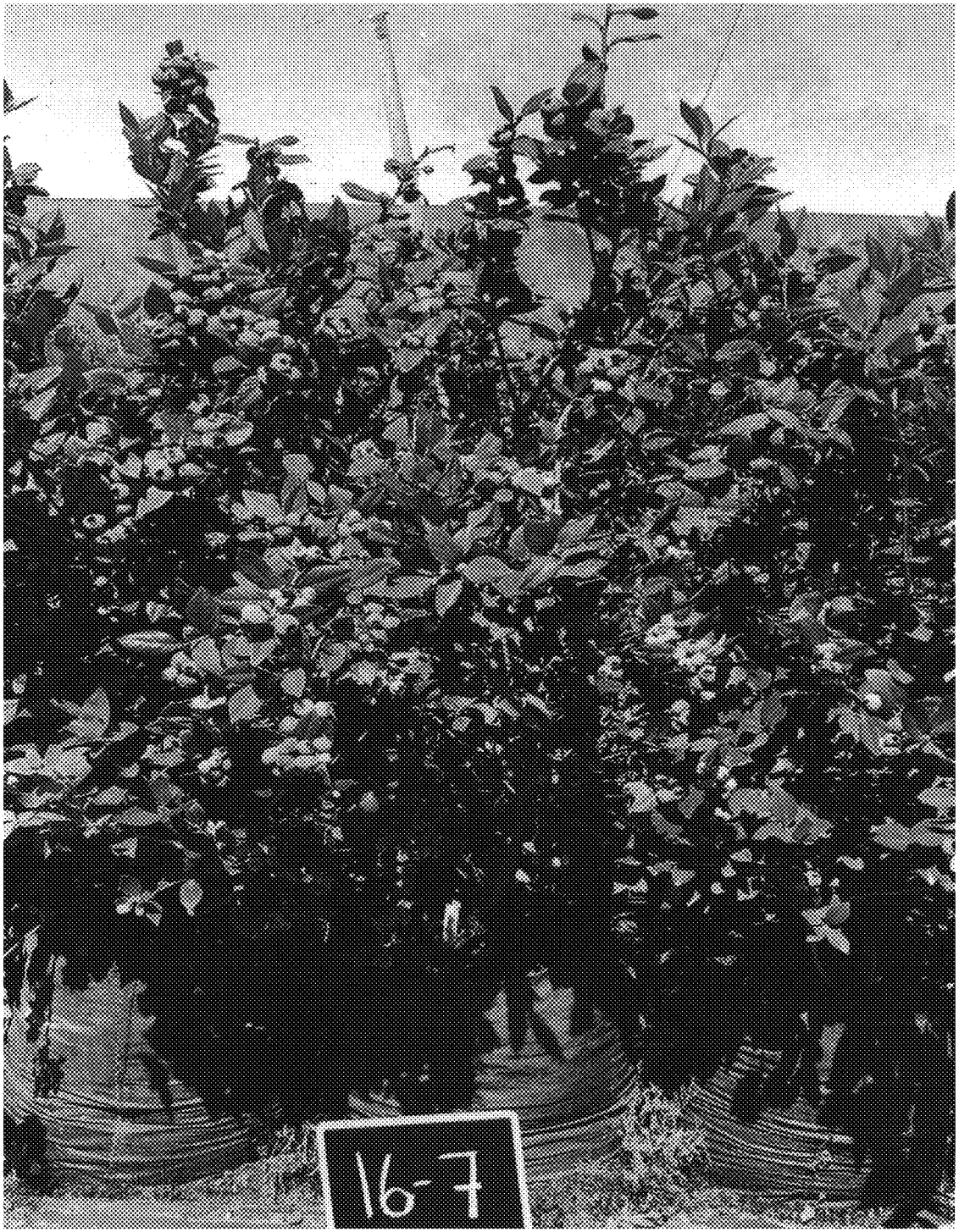
FIG. 2 is a color photograph, which shows the new blueberry plant 'NS 16-7'. This photograph depicts a mature bush with ripe and unripe fruits, the fruit size, and the upright growth habit of the bush. The ripe fruit is sufficiently mature for harvesting and shipment.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Sixth Edition (2015), hereinafter, "R.H.S.") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of blueberry plant, the following has been observed during the second year of growth under the ecological conditions prevailing at the breeder's property, which is located at Yanchep Springs in Yanchep, Western Australia.

Plant: General.

*Vigor*.—Considered strong for the species. This is in contrast to the seed parent 'EB 8-42', wherein the vigor is considered to be medium to strong. This is also in contrast to the pollen parent 'EB 9-2', the closest known variety, wherein the vigor is considered to be strong to very strong.

*Growth habit*.—Considered upright, in like manner to the commercial variety 'Ivanhoe' (unpatented).

*Average size of plant*.—1.5 meters in height by 1.1 meters in width.

*Internode length* (*space between nodes*).—Considered medium, 19.23 millimeters (mm).

*Bark color*.—RHS Dark Greyish Yellowish Brown Group N199C.

*Color, one year old shoots*.—RHS Moderate Yellow Green Group N148B.

*Fruiting type*.—On one-year-old shoots only, in like manner to commercial varieties 'Darrow' (unpatented) and 'Patriot' (unpatented).

Foliage: General.

*Average leaf length*.—Considered medium for the species, 56.95 mm.

*Average leaf width*.—Considered medium for the species, 25.9 mm.

*Color of leaf upper*.—RHS Greyish Olive Green Group NN137B.

*Color of leaf underside*.—RHS Moderate Yellow Green Group 148B.

*Vein color of plant leaf*.—RHS Light Yellow Green Group 145B.

*Venation pattern of leaf*.—Pinnate reticulate.

*Leaf apex texture*.—Glabrous.

*Leaf apex shape*.—Acute.

*Leaf base shape*.—Acute.

*Leaf shape*.—Elliptic.

*Leaf margin*.—Entire.

*Leaf arrangement of plant*.—Alternate.

*Petiole length*.—3.45 mm.

*Petiole diameter*.—2.26 mm.

*Petiole color*.—RHS Light Yellow Green 145B.

Flowers:

*Number of flowers/inflorescence*.—7-10.

*Length of inflorescence* (*excluding pedicel*).—Considered long to very long, 12.34 mm.

*Corolla shape*.—Urceolate.

*Corolla tube surface texture*.—Ridges are present on the corolla tube.

*Average corolla length*.—9.2 mm.

*Corolla diameter*.—7.22 mm.

*Corolla aperture size*.—4.35 mm.

*Corolla color*.—RHS Greenish White Group 155C.

*Pedicel color*.—RHS Strong Yellow Green Group 144C.

*Pedicel length*.—8.58 mm.

*Average calyx diameter*.—Considered medium to large, 6.61 mm.

*Average calyx basin depth*.—Considered deep, 3.62 mm.

*Attitude of sepals*.—Erect.

*Type of sepals*.—Straight.

Reproductive organs:

*Size of pollen anthers*.—6.34 mm.

*Color of pollen anthers*.—RHS Moderate Reddish Orange Group N172B.

*Pistil length*.—9.88 mm.

*Pistil color*.—RHS Light Yellow Green Group 145B.

Fruit:

*Color of unripe fruit*.—RHS Light Yellow Green Group 145B.

*Color of fruit skin*.—RHS Bluish Black Group 203C, also considered "dark blue" in like color to the commercial variety 'Heerma' (unpatented), after removal of bloom.

*Color of ripe fruit flesh*.—RHS Light Yellow Green Group 145D.

*Color of seeds*.—RHS Greyish Reddish Brown Group 200B.

*Average fruit size*.—Large, 18 mm in diameter and 14.33 mm in height. This is comparable to the seed parent 'EB 8-42', wherein the fruit size is also considered large. This is in contrast to the pollen parent 'EB 9-2', the closest known variety, wherein the fruit size is considered large to very large.

*Average weight of fruit*.—3.0 grams.

*Berry shape*.—Considered oblate.

*Sweetness when ripe*.—Considered high to very high for the species. This is in contrast to the seed parent 'EB 8-42', wherein the fruit sweetness is considered medium to high. This is also in contrast to the pollen parent 'EB 9-2', the closest known variety, wherein the fruit sweetness is considered high.

*Firmness when ripe*.—Considered firm for the species. This is comparable to the seed parent 'EB 8-42', wherein the fruit firmness is also considered firm. This is in contrast to the pollen parent 'EB 9-2', the closest known variety, wherein the fruit firmness is considered firm to very firm.

*Acidity when ripe*.—Considered very low for the species.

*Cluster density*.—Considered dense for the species.

*Average fruit production*.—3.5 kilograms on a two-year-old bush.

*Storability of fruit*.—Considered excellent for the species.

*Market use of fruit*.—1st grade fresh market fruit.

*Date of bud burst*.—This variety is evergreen under the ecological conditions prevailing in Yanchep, Western Australia, but a bud break occurs in late June.

*Date of bloom time*.—This variety is evergreen under the ecological conditions prevailing in Yanchep, Western Australia, but a bloom time occurs in late July/August, which is considered medium to late on one-year-old shoot after the commercial variety 'Berkeley' (unpatented), which is medium, but before the commercial variety 'Darrow' (unpatented), which is late.

*Duration of bloom time*.—3 weeks.

*Beginning of fruit ripening*.—Considered medium to late on one-year-old shoot after the commercial variety 'Heema' (unpatented), which is medium, but before the commercial variety 'Darrow' (unpatented), which is late.

*First pick date*.—The observed date of the first pick is approximately November under the ecological conditions prevailing in Yanchep, Western Australia.

*Last pick date*.—The observed date of the last pick is approximately mid-December under the ecological conditions prevailing in Yanchep, Western Australia.

*Pollination requirements*.—Self-fertile.

*Resistance to pests and disease*.—No particular resistance noted. The variety has not been tested to detect any resistance.

Although the new variety of blueberry plant possesses the described characteristics when grown under the ecological conditions prevailing in Yanchep, Western Australia, it should be understood that variations are to be expected in the usual magnitude and characteristics incident to changes in growing conditions, fertilization, pruning, pest control, frost, climatic variables, and horticultural management.

Having thus described and illustrated a new variety of blueberry plant, what is claimed to secure a plant Letters Patent is:

1. A new and distinct variety of blueberry plant, substantially as illustrated and described, which is characterized principally as to novelty by a strong plant vigor and by producing fruit considered large in size, high to very high in sweetness, and firm under the ecological conditions prevailing in Yanchep, Western Australia.

* * * * *